United States Patent
Chu (10) Patent No.: US 9,486,210 B2
(45) Date of Patent: Nov. 8, 2016

(54) SUTURING INSTRUMENT AND METHOD FOR UTERINE PRESERVATION

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 64 days.

(21) Appl. No.: 14/324,866

(22) Filed: Jul. 7, 2014

(65) Prior Publication Data

US 2014/0324075 A1    Oct. 30, 2014

Related U.S. Application Data

(63) Continuation of application No. 12/434,038, filed on May 1, 2009, now Pat. No. 8,771,295.

(60) Provisional application No. 61/060,556, filed on Jun. 11, 2008.

(51) Int. Cl.
*A61B 17/04* (2006.01)
*A61B 17/12* (2006.01)

(52) U.S. Cl.
CPC ...... *A61B 17/0469* (2013.01); *A61B 2017/047* (2013.01); *A61B 2017/0472* (2013.01)

(58) Field of Classification Search
CPC ............ A61B 17/04; A61B 17/0469; A61B 17/0483; A61B 17/06; A61B 2017/047; A61B 17/0491; A61B 17/0493
See application file for complete search history.

(56) References Cited

U.S. PATENT DOCUMENTS

| 342,773 | A | 6/1886 | Bailey |
| 919,138 | A | 4/1909 | Drake et al. |
| 1,037,864 | A | 9/1912 | Carlson et al. |
| 1,449,087 | A | 3/1923 | Bugbee |
| 1,815,725 | A | 7/1931 | Pilling et al. |
| 1,822,330 | A | 9/1931 | Ainslie |
| 2,577,240 | A | 12/1951 | Findley |
| 2,579,192 | A | 12/1951 | Kohl |

(Continued)

FOREIGN PATENT DOCUMENTS

| EP | 0140557 A2 | 5/1985 |
| EP | 0589409 A1 | 3/1994 |

(Continued)

OTHER PUBLICATIONS

International Search Report and Written Opinion for PCT Patent Application No. PCT/US2009/042489, mailed on Sep. 2, 2009, 4 pages.

(Continued)

*Primary Examiner* — Melanie Tyson
(74) *Attorney, Agent, or Firm* — Brake Hughes Bellermann LLP (57) ABSTRACT

A suturing instrument includes an elongate body member, a needle deployment mechanism, and a depth adaptor. The elongate body member includes a distal portion that defines an opening. The needle deployment mechanism is at least partially disposed within the elongate body member and moves the needle out of the suturing instrument and into tissue. The depth adaptor is disposed in the opening at the distal portion of the elongate body member and controls the depth that the needle penetrates into the tissue.

19 Claims, 12 Drawing Sheets

(56) References Cited

U.S. PATENT DOCUMENTS

| | | |
|---|---|---|
| 3,013,559 A | 12/1961 | Thomas |
| 3,160,157 A | 12/1964 | Chisman |
| 3,470,875 A | 10/1969 | Johnson |
| 3,557,780 A | 1/1971 | Sato |
| 3,638,653 A | 2/1972 | Berry |
| 3,840,017 A | 10/1974 | Violante |
| 3,918,455 A | 11/1975 | Coplan |
| 3,946,740 A | 3/1976 | Bassett |
| 3,986,468 A | 10/1976 | Szostak et al. |
| 4,161,951 A | 7/1979 | Scanlan, Jr. |
| 4,164,225 A | 8/1979 | Johnson et al. |
| 4,224,947 A | 9/1980 | Fukuda |
| 4,235,177 A | 11/1980 | Arbuckle |
| 4,235,238 A | 11/1980 | Ogiu et al. |
| 4,236,470 A | 12/1980 | Stenson |
| 4,312,337 A | 1/1982 | Donohue |
| 4,345,601 A | 8/1982 | Fukuda |
| 4,493,323 A | 1/1985 | Albright et al. |
| 4,548,202 A | 10/1985 | Duncan |
| 4,557,265 A | 12/1985 | Andersson |
| 4,579,072 A | 4/1986 | Koike et al. |
| 4,596,249 A | 6/1986 | Freda et al. |
| 4,602,635 A | 7/1986 | Mulhollan et al. |
| 4,621,640 A | 11/1986 | Mulhollan et al. |
| 4,635,638 A | 1/1987 | Weintraub et al. |
| 4,762,260 A | 8/1988 | Richards et al. |
| 4,781,190 A | 11/1988 | Lee |
| 4,890,615 A | 1/1990 | Caspari et al. |
| 4,898,155 A | 2/1990 | Ovil et al. |
| 4,899,746 A | 2/1990 | Brunk |
| 4,923,461 A | 5/1990 | Caspari et al. |
| 4,926,860 A | 5/1990 | Stice et al. |
| 4,935,027 A | 6/1990 | Yoon |
| 4,957,498 A | 9/1990 | Caspari et al. |
| 5,037,433 A | 8/1991 | Wilk et al. |
| 5,042,707 A | 8/1991 | Taheri |
| 5,047,039 A | 9/1991 | Avant et al. |
| 5,067,957 A | 11/1991 | Jervis |
| 5,100,415 A | 3/1992 | Hayhurst |
| 5,100,418 A | 3/1992 | Yoon et al. |
| 5,100,421 A | 3/1992 | Christoudias |
| 5,100,498 A | 3/1992 | Takeuchi et al. |
| 5,188,636 A | 2/1993 | Fedotov |
| 5,258,011 A | 11/1993 | Drews |
| 5,281,237 A | 1/1994 | Gimpelson |
| 5,306,281 A | 4/1994 | Beurrier |
| 5,308,353 A | 5/1994 | Beurrier |
| 5,324,298 A | 6/1994 | Phillips et al. |
| 5,336,231 A | 8/1994 | Adair |
| 5,364,408 A | 11/1994 | Gordon |
| 5,387,221 A | 2/1995 | Bisgaard |
| 5,389,103 A | 2/1995 | Melzer et al. |
| 5,391,174 A | 2/1995 | Weston |
| 5,417,699 A | 5/1995 | Klein et al. |
| 5,417,700 A | 5/1995 | Egan |
| 5,454,823 A | 10/1995 | Richardson et al. |
| 5,458,609 A | 10/1995 | Gordon et al. |
| 5,522,820 A | 6/1996 | Caspari et al. |
| 5,527,321 A | 6/1996 | Hinchliffe |
| 5,540,704 A | 7/1996 | Gordon et al. |
| 5,540,705 A | 7/1996 | Meade et al. |
| 5,549,617 A | 8/1996 | Green et al. |
| 5,549,637 A | 8/1996 | Crainich |
| 5,562,686 A | 10/1996 | Sauer et al. |
| 5,573,542 A | 11/1996 | Stevens |
| 5,575,800 A | 11/1996 | Gordon |
| 5,578,044 A | 11/1996 | Gordon et al. |
| 5,591,179 A | 1/1997 | Edelstein |
| 5,593,421 A | 1/1997 | Bauer |
| 5,662,664 A | 9/1997 | Gordon et al. |
| 5,662,666 A | 9/1997 | Onuki et al. |
| 5,665,096 A | 9/1997 | Yoon |
| 5,690,653 A | 11/1997 | Richardson et al. |
| 5,700,272 A | 12/1997 | Gordon et al. |
| 5,700,273 A | 12/1997 | Buelna et al. |
| 5,713,910 A | 2/1998 | Gordon et al. |
| 5,741,277 A | 4/1998 | Gordon et al. |
| 5,741,279 A | 4/1998 | Gordon et al. |
| 5,755,727 A | 5/1998 | Kontos |
| 5,759,188 A | 6/1998 | Yoon |
| 5,779,718 A | 7/1998 | Green et al. |
| 5,782,845 A | 7/1998 | Shewchuk |
| 5,827,298 A | 10/1998 | Hart et al. |
| 5,843,001 A | 12/1998 | Goldenberg |
| 5,855,585 A | 1/1999 | Kontos |
| 5,860,992 A | 1/1999 | Daniel et al. |
| 5,899,909 A | 5/1999 | Claren et al. |
| 5,904,692 A | 5/1999 | Steckel et al. |
| 5,908,428 A | 6/1999 | Scirica et al. |
| 5,911,727 A | 6/1999 | Taylor |
| 5,919,199 A | 7/1999 | Mers Kelly et al. |
| 5,954,732 A | 9/1999 | Hart et al. |
| 6,048,351 A | 4/2000 | Gordon et al. |
| 6,051,006 A | 4/2000 | Shluzas et al. |
| 6,117,067 A | 9/2000 | Gil-Vernet |
| 6,224,525 B1 | 5/2001 | Stein |
| 6,443,962 B1 | 9/2002 | Gaber |
| 6,454,778 B2 | 9/2002 | Kortenbach |
| 6,743,239 B1 | 6/2004 | Kuehn et al. |
| 7,232,447 B2 | 6/2007 | Gellman et al. |
| 7,628,796 B2 | 12/2009 | Shelton, IV et al. |
| 7,666,195 B2* | 2/2010 | Kelleher ............ A61B 17/0218 606/139 |
| 8,771,295 B2 | 7/2014 | Chu |
| 2005/0055038 A1 | 3/2005 | Kelleher et al. |
| 2009/0171143 A1* | 7/2009 | Chu .................. A61B 17/0401 600/37 |
| 2009/0312772 A1 | 12/2009 | Chu |

FOREIGN PATENT DOCUMENTS

| | | |
|---|---|---|
| EP | 0674875 A1 | 10/1995 |
| GB | 2268690 A | 1/1994 |
| WO | 90/03766 A1 | 4/1990 |
| WO | 92/12674 A1 | 8/1992 |
| WO | 93/01750 A1 | 2/1993 |
| WO | 94/05213 A1 | 3/1994 |
| WO | 94/13211 A1 | 6/1994 |
| WO | 96/09796 A2 | 4/1996 |
| WO | 96/27331 A1 | 9/1996 |
| WO | 99/47050 A2 | 9/1999 |
| WO | 01/28432 A1 | 4/2001 |
| WO | 2008/058067 A1 | 5/2008 |
| WO | 2010/011306 A1 | 1/2010 |

OTHER PUBLICATIONS

International Preliminary Report on Patentability for PCT Patent Application No. PCT/US2009/042489, mailed on Dec. 23, 2010, 8 pages.
Restriction Requirement for U.S. Appl. No. 12/434,038, mailed on May 16, 2011, 7 pages.
Response to Restriction Requirement for U.S. Appl. No. 12/434,038, filed Jun. 15, 2011, 1 page.
Non-Final Office Action for U.S. Appl. No. 12/434,038, mailed on Jun. 29, 2011, 7 pages.
Response to Non-Final Office Action for U.S. Appl. No. 12/434,038, filed Sep. 15, 2011, 6 pages.
Final Office Action for U.S. Appl. No. 12/434,038, mailed on Nov. 3, 2011, 8 pages.
Response to Final Office Action for U.S. Appl. No. 12/434,038, filed Dec. 23, 2011, 7 pages.
Notice of Allowance for U.S. Appl. No. 12/434,038, mailed on Feb. 25, 2014, 5 pages.

* cited by examiner

SUTURING INSTRUMENT AND METHOD FOR UTERINE PRESERVATION

CROSS-REFERENCE TO RELATED APPLICATIONS

This application is a Continuation of, and claims priority to, U.S. patent application Ser. No. 12/434,038, filed on May 1, 2009, entitled "SUTURING INSTRUMENT AND METHOD FOR UTERINE PRESERVATION", which claims priority to and the benefit of, U.S. Provisional Application No. 61/060,556, filed on Jun. 11, 2008, the disclosures of which are incorporated by reference herein in their entirety.

TECHNICAL FIELD

The invention relates generally to devices and methods for placing sutures, and in particular to devices and methods for treating various pelvic dysfunctions including procedures to repair uterine prolapse, cystoceles, rectoceles, and vaginal vault prolapse.

BACKGROUND INFORMATION

Suturing of body tissue is a time consuming aspect of many surgical procedures. For many surgical procedures, it is necessary to make a large opening in the human body to expose the area that requires surgical repair. There are instruments available that allow for viewing of certain areas of the human body through a small puncture wound without exposing the entire body cavity. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

In various corrective surgeries or implant procedures, bodily tissue must be returned to a normal anatomical position or placed in an improved position. For example, when uterine prolapse occurs, weakened ligaments cause the uterus to descend into the vaginal cavity. One way to correct uterine prolapse requires that the vaginal apex be approximated to the sacrospinous ligament. The uterus is suspended by sutures that are passed through the vaginal wall. In certain circumstances such as, for example, grade two prolapse (small prolapse), passing sutures through the vaginal wall with a free needle and needle driver is often difficult as there is limited space to work in.

A vaginal prolapse can be due to age or other factors and typically results in one of three types of prolapse: hysterocele, cystocele, and rectocele. A hysterocele occurs when the uterus descends into the. A cystocele prolapse occurs when the bladder bulges or descends into the vagina and a rectocele occurs when the rectum bulges or descends into the vagina. It is often common for more than one of a hysterocele and cystocele, a hysterocele and a rectocele to occur at the same time. Treatment of vaginal vault prolapse, including a vaginal prolapse due to a hysterocele, can include a suturing procedure or the use of an implant for support or suspension.

Another procedure to treat a prolapse caused by a hysterocele is to perform a hysterectomy. Many patients, however, want to avoid a hysterectomy for a variety of reasons, including plans for future childbearing, concern about the invasiveness of the procedure, the difficulty of the recuperation, or fear of diminished sexual function. Some women are simply reluctant to "give up" this part of their body so closely associated with their reproductive health, childbearing, and femininity.

Uterine prolapse can be effectively treated without hysterectomy, with low morbidity and high rates of patient satisfaction. A properly performed uterine suspension procedure often results in a significantly better anatomic outcome than a hysterectomy. Yet, many hysterectomy procedures are performed for pelvic prolapse. Many patients remain unaware of uterine-sparing options because with the exception of a few dedicated sub-specialists, most surgeons receive no training in these techniques. In addition, known techniques can be difficult, and can require specialized training that many general practitioners have not undertaken.

SUMMARY OF THE INVENTION

Devices and methods for performing various medical procedures within a pelvic region of a patient are described herein. For example, medical procedures to treat uterine prolapse, vaginal vault prolapse, rectocele, and cystocele are described herein.

In one aspect, the invention is directed to a suturing instrument including an elongate body member, a needle deployment mechanism, and a depth adaptor. The elongate body member includes a distal portion that defines an opening. The needle deployment mechanism is at least partially disposed within the elongate body member. The needle deployment mechanism is configured to move a needle out of the suturing instrument and into tissue of a patient. The depth adaptor is disposed in the opening at the distal portion of the elongate body member and controls the depth that the needle penetrates into the tissue.

In various embodiments, the suturing instrument may further include a needle catch disposed on the distal portion of the elongate body member. The needle catch is configured to receive the needle. In one embodiment, the needle deployment mechanism may also include a needle carrier, and an actuator coupled to the needle carrier. The actuator may be disposed at least partially in a proximal portion of the elongate body member.

In additional embodiments, the elongate body member includes one or more bends. The suturing instrument can be adapted to access remote organs or tissue within a body. The distal portion of the elongate body member can be rotatable relative to a remainder of the elongate body member. Further, the suturing instrument may include a handle disposed opposite the distal portion of the elongate body member. The handle can at least partially house the needle deployment mechanism. The suturing instrument can be used, for example, to access areas within the patient's body to ligate, fixate, or approximate tissue.

In a further aspect, the invention is directed to a suturing instrument including an elongate body member, a needle deployment mechanism, and a plurality of depth adaptors. The elongate body member includes a distal portion that defines an opening. The needle deployment mechanism is at least partially disposed within the elongate body member and is configured to move a needle out of the suturing instrument and into tissue of a patient. Each of the plurality of depth adaptors is capable of being removably disposed in the opening to control the penetration depth of the needle. Further, each of the plurality of depth adaptors allows the needle to penetrate a tissue at a different penetration depth and can include a color or other markings to identify its size or penetrating depth.

In various embodiments, the suturing instrument may further include a needle deployment mechanism. The needle deployment mechanism is coupled to the needle and is at least partially disposed within the elongate body member. The needle deployment mechanism moves the needle out of the suturing instrument and into tissue. In one embodiment, the needle deployment mechanism may also include a needle carrier, and an actuator coupled to the needle carrier. The actuator may be disposed at least partially in a proximal portion of the elongate body member.

In additional embodiments, the elongate body member includes one or more bends. The suturing instrument can be adapted to access remote organs or tissue within a body. The distal portion of the elongate body member can be rotatable relative to a remainder of the elongate body member. Further, the suturing instrument may include a handle disposed opposite the distal portion of the elongate body member. The handle can at least partially house the needle deployment mechanism.

Disclosed suturing instruments can be used to perform various medial procedures within a pelvic region of a patient. In one embodiment, a suturing instrument is used to secure a suture to the sacrospinous ligament on a one side of the pelvic region. The suturing instrument then can be used to secure a second suture the sacrospinous ligament on the opposite side of the pelvic region. The first suture is then secured to the vaginal apex at a first location and the second suture is secured to the vaginal apex at a second location. Finally, the two sutures are tensioned such that the vaginal apex is approximated to the sacrospinous ligaments on either side of the pelvic region. The suture preferably does not penetrate through the entire thickness of the vaginal wall such that the two ends of the suture can be knotted within an anterior incision instead of within the vaginal lumen.

BRIEF DESCRIPTION OF THE DRAWINGS

A fuller understanding of the aspects, objects, features, and advantages of certain embodiments according to the invention will be obtained and understood from the following description when read together with the accompanying drawings, which primarily illustrate the principles of the invention and embodiments thereof. The drawings are not necessarily to scale and like reference characters denote corresponding or related parts throughout the several views. The drawings and the disclosed embodiments of the invention are exemplary only and not limiting on the invention.

DESCRIPTION

Figure 1A:
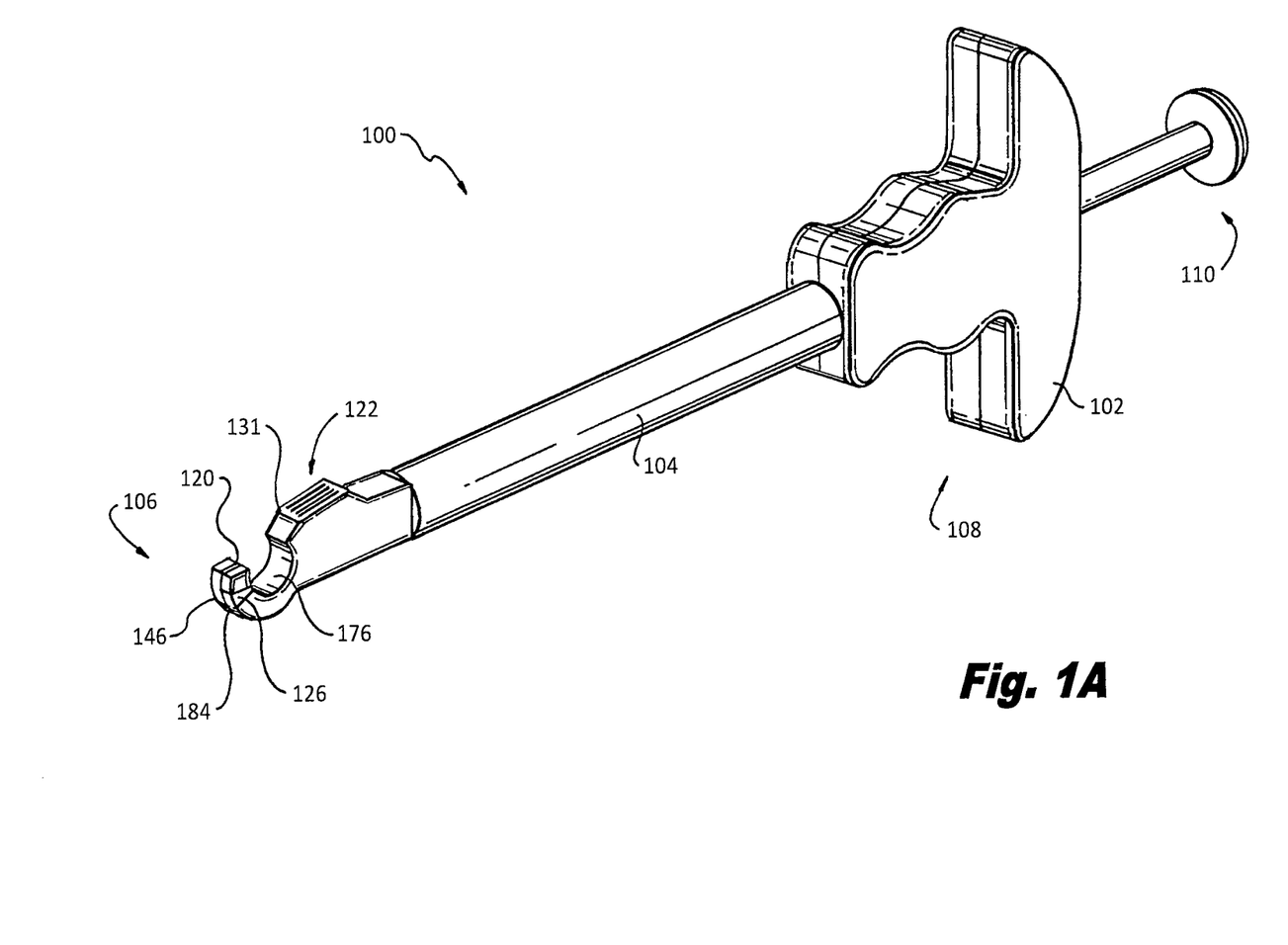
FIG. 1A is a schematic perspective view of one embodiment of a suturing instrument in accordance with the invention.

As indicated above, the present invention relates to devices and methods for treating various pelvic dysfunctions including repairing uterine prolapse, cystoceles, rectoceles, and vaginal vault prolapse. FIG. 1A depicts a suturing instrument 100 including a handle 102, an elongate body member 104, and a needle deployment mechanism 110. The suturing instrument could take a variety of forms. For example, the suturing instrument 100 could be one of Boston Scientific Corporation suturing instrument, in particular, the Capio® Open Access and Standard Suture Capturing Devices. The suturing instrument 100 also includes a distal portion 106 and a proximal portion 108. The elongate body member 104 is mechanically coupled to the handle 102 at the proximal portion 108, and the suturing components are at least partially disposed within the distal portion 106 of the suturing instrument 100.

Figure 3A:
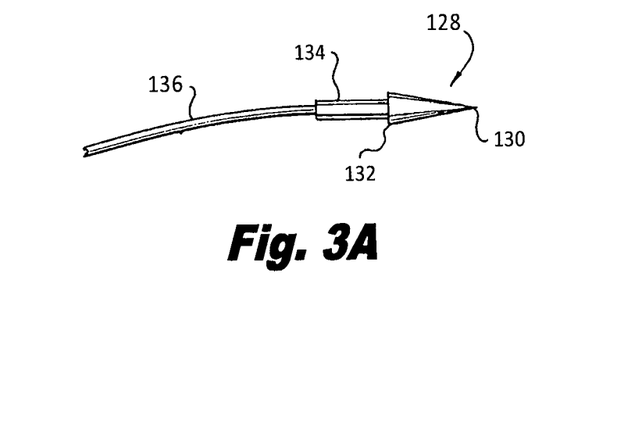
FIG. 3A is a schematic plan view of a needle coupled to a suture for use in a suturing instrument in accordance with the invention.

The handle 102 could take a variety of forms, for example, the handle 102 could be one of the types used with Boston Scientific Corporation suturing systems, in particular the Capio® Push & Catch suturing system. Generally, the needle deployment mechanism 110 extends longitudinally through the elongate body member 104 to the distal portion 106 of the suturing instrument 100, where the needle deployment mechanism 110 is coupled to a needle 128 (FIG. 3A). The needle deployment mechanism 110 moves the needle 128 between a retracted position and a deployed position. The needle deployment mechanism 110 is shown in greater detail in FIGS. 1B and 1C.

Figure 1B:
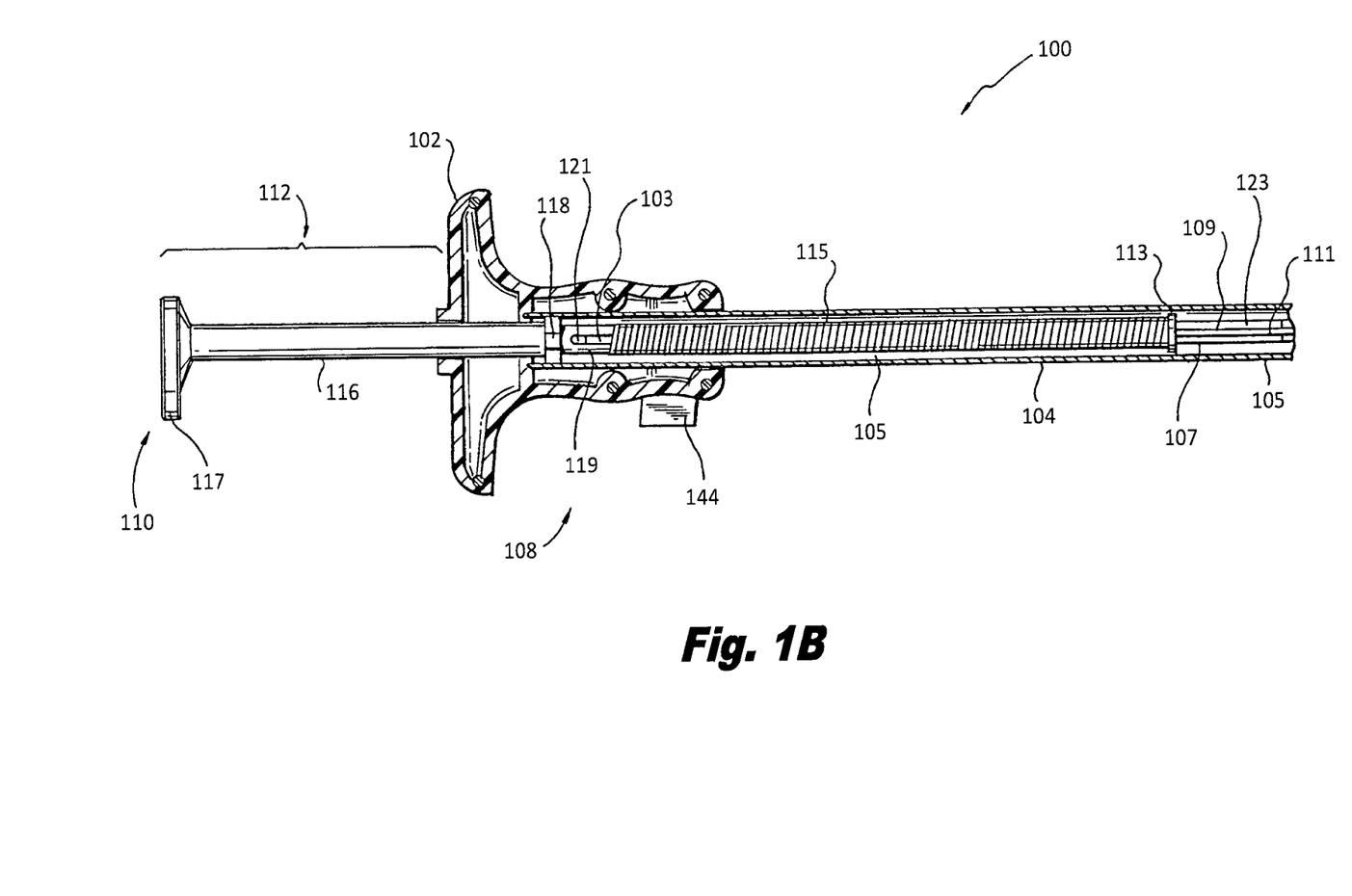
FIG. 1B is a schematic cross-sectional views of the proximal portion of the suturing instrument of FIG. 1A.

Referring to FIG. 1B, the proximal portion 108 of the suturing instrument 100 includes the handle 102, the elongate body member 104, a suture clip 144, and the needle deployment mechanism 110. The suture clip 144 may be coupled to the handle 102 or the elongate body member 104 and is used to hold an end of one or more sutures prior to placement in a patient. The needle deployment mechanism 110 includes an actuator 112 (button 117, shaft 116), a bearing 118, a button end 119, and a hole 121. The bearing 118 rides along a cylindrical surface 105 that is formed by the inside diameter of the elongate body member 104. A wireform 103 is inserted into the hole 121, coupling it to the actuator button 117. A spring 115 encircles the wireform 103, abuts the button end 119, and is compressed between the button end 119 and a spring washer 113. The spring washer 113 is seated upon a center tube 107. The center tube 107 is housed by the cylindrical surface 105 and is constrained in the distal portion 106. A pusher wire 111 is attached to the wireform 103 by means of a weld, a coupling, adhesive or other means, and is slidably disposed within a guidance sleeve 109, the sleeve 109 being disposed within a cylindrical surface 123 formed by the inside diameter of the center tube 107. In one embodiment, the pusher wire 111 is constructed of Nitinol (nickel-titanium alloy), so chosen for its combination of properties that allow for bendability and high column strength when constrained.

Figure 1C:
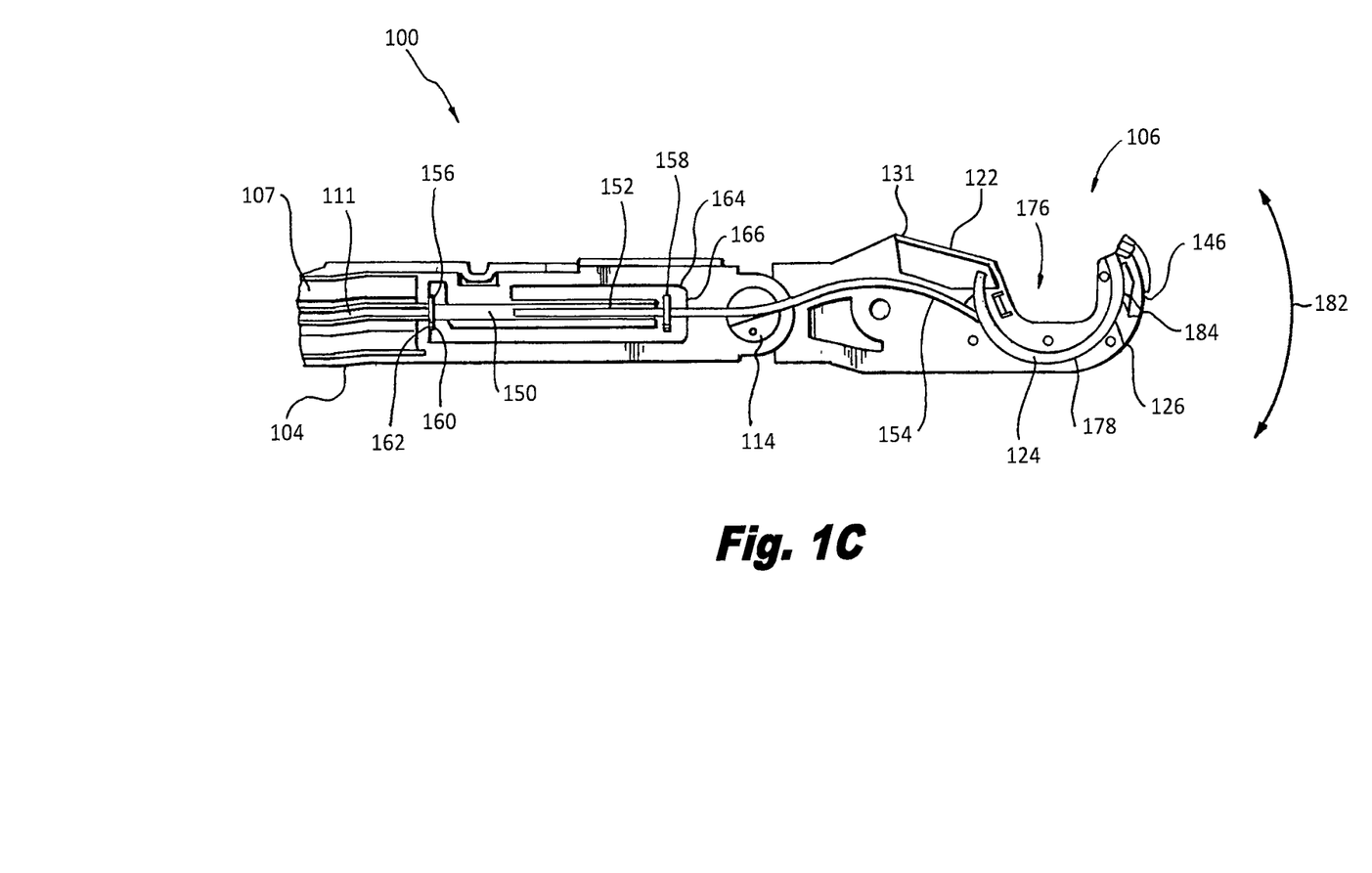
FIG. 1C is a schematic cross-sectional view of a distal portion of a suturing instrument in accordance with one exemplary embodiment of the invention.

Referring to FIG. 1C, the distal portion 106 of the elongate body member 104 includes a raised portion (or protuberance) 131 and a curved portion 126 including a knot pusher 184. The raised portion 131 includes a needle catch 122. The curved portion 126 defines a needle exit port 120 and a suture slot 146. The curved portion 126 also defines an opening 176 for receiving tissue. Referring again to the needle deployment mechanism 110, the pusher wire 111 is attached by welding or other means to a coupling 150, which is slidably disposed within a track 152. The coupling 150 is attached to a carrier wire 154, which by virtue of its attachment to the coupling 150 is also slidably disposed within the track 152. The carrier wire 154 is mechanically coupled to an extendable needle carrier 124 by means of a weld, a coupling, adhesives, or other means. The coupling 150 abuts a backstop washer 156 that is slidably disposed about the pusher wire 111 and is contained within a pocket 160 that includes a back wall 162, against which the backstop washer 156 rests. The track 152 terminates distally in a pocket 164 that includes a wall 166. A downstop washer 158 is slidably disposed about the carrier wire 154 and constrained within the pocket 164.

In some embodiments, the suturing instrument 100 may include the articulation mechanism 114. The articulation mechanism 114 is disposed in the elongate body member 104 proximate the distal portion 106 (FIG. 1C). The articulation mechanism 114 facilitates the rotation (in the directions indicated by arrow 182) and positioning of the distal end 106 of the suturing instrument 100. In addition, the elongate body 104 can be substantially linear or may include one or more bends. The articulation mechanism 114 and/or bend(s) can facilitate access to deep and/or difficult to reach areas within the patient.

Figure 2A:
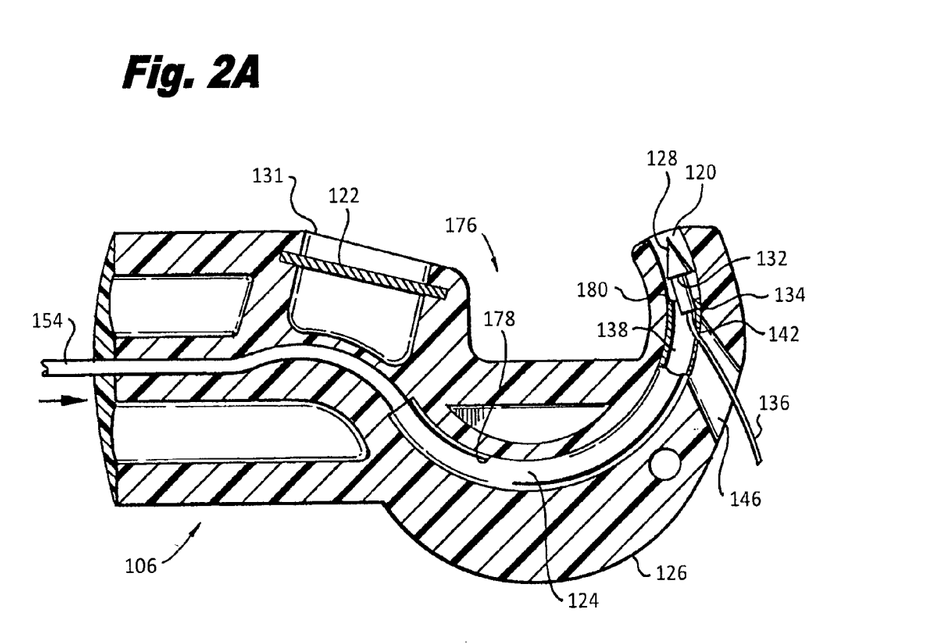
FIGS. 2A and 2B are enlarged cross-sectional views of the distal portion of the suturing instrument of FIG. 1A.
Figure 2B:
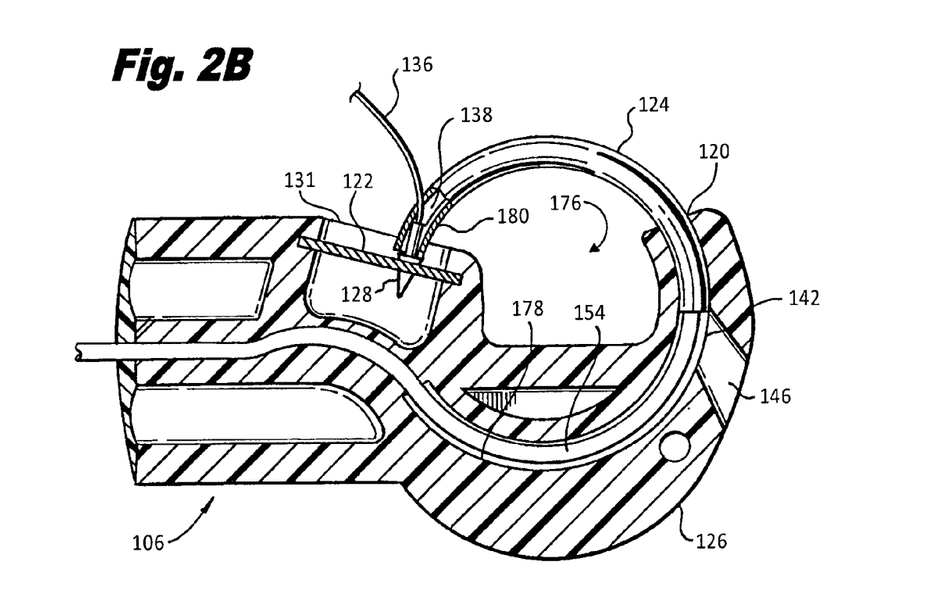
Figure 2C:
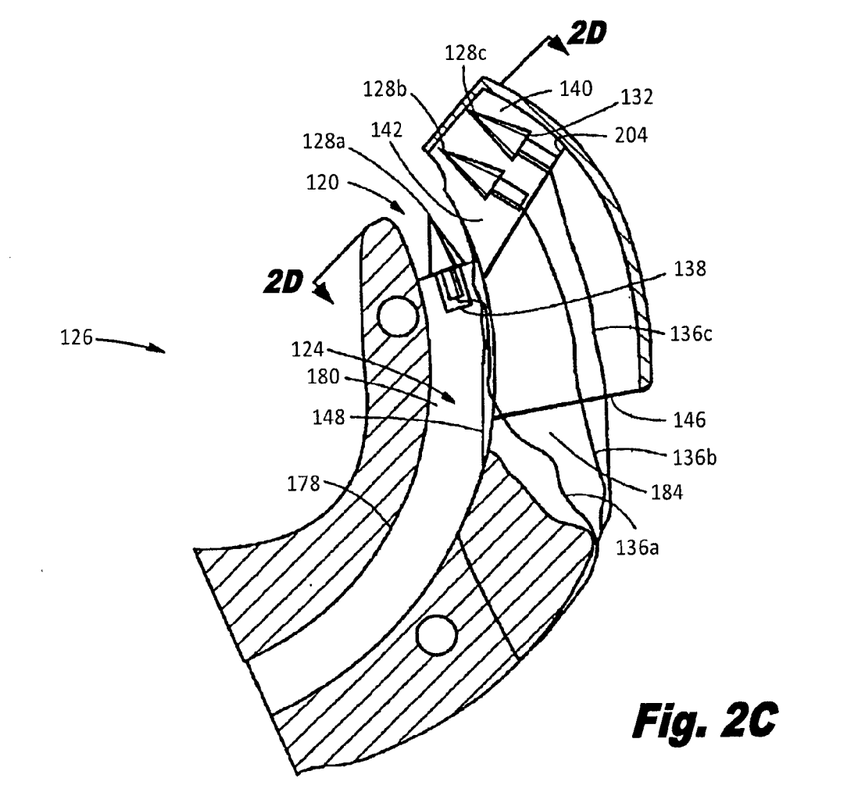
FIG. 2C is an enlarged cross-sectional view of alternative embodiment of a suturing instrument in accordance with the invention.
Figure 2D:
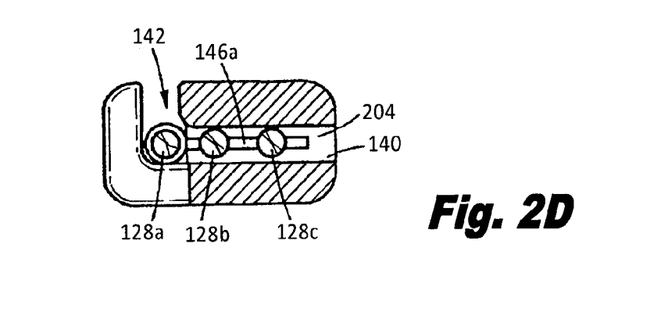
FIG. 2D is a schematic top view of the suturing instrument of FIG. 2C taken at line D-D.

Referring to FIGS. 2A and 2B, in one embodiment, the curved portion 126 defines a channel 178, an opening (or needle exit port 120), a needle input/output slot 142, and a suture slot 146. A needle carrier 124 is disposed within the channel 178 in the curved portion 126. A distal portion 180 of the needle carrier 124 defines a lumen 138 for holding a needle 128. The curved portion 126 also defines an opening 176 for receiving tissue. In an alternative embodiment (FIGS. 2C and 2D), the curved portion 126 defines a tunnel or needle compartment 140 for holding a plurality of needles 128a, 128b, 128c (generally needle 128).

Referring to FIG. 3A, in one embodiment, the needle 128 includes a tip 130 and a shaft 134 coupled to the tip 130, thereby forming a shoulder 132. The shaft 134 is coupled to a suture 136a, 136b, 136c (generally suture 136). The needle 128 is inserted into the lumen 138 and held by a slight friction fit. The suture 136 extends out of a needle carrier suture slot 148 and the suture slot 146. Needles 128b and 128c are stored in the needle compartment 140 prior to being deployed.

Figure 3B:
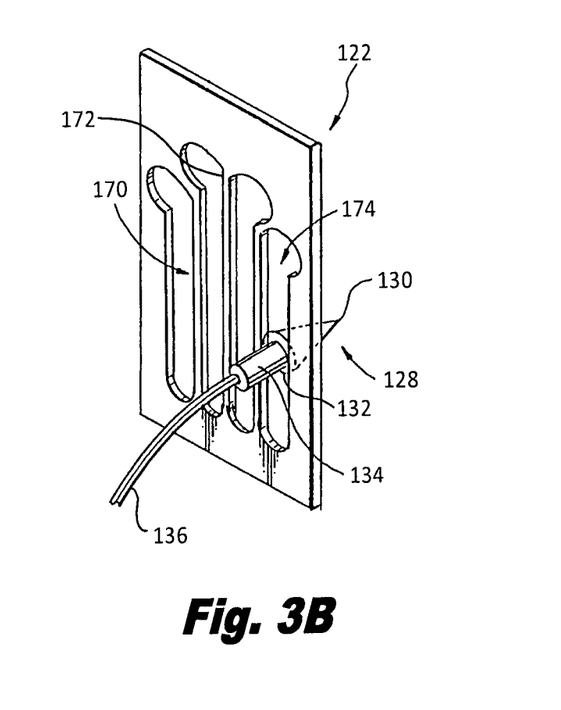
FIG. 3B is a schematic perspective view of a needle catch for use with the suturing instrument of FIG. 1A.

Referring again to FIGS. 1B, 1C, 2A, and 2B, in operation, a user (such as a physician or other medical personnel) actuates the needle deployment mechanism 110 by pushing on the button 117, which via the attachment to the wireform 103 which is attached to the pusher wire 111, moves the coupling 150 along the track 152 concomitantly moving the carrier wire 154, which slidably moves the needle carrier 124 through the needle exit port 120. The user continues to push the button 117 until the needle 128 enters the needle catch 122. The needle catch 122, as shown in FIG. 3B, includes openings 170 defined by successive ribs 172. The needle catch 122 receives the needle 128 (coupled to the suture 136) through opening 170, the ribs 172 deflect slightly to allow the needle 128 to pass through. After the formed shoulder 132 has passed the ribs 172, the ribs 172 spring back to their original position defining the openings 170, and the needle 128 remains captured in the needle catch 122. The user releases the button 117 and the spring 115 urges the button 117 proximally, moving the pusher wire 111, the coupling 150, the carrier wire 154, and the needle carrier 124 proximally along with the button 117 to the retracted position. As the needle carrier 124 moves back to the retracted position, the needle 128 slides out of the lumen 138. The openings 170 are chosen to be smaller in dimension than the formed shoulder 132. This causes the needle catch 122 to retain the needle 128 because the flat rear surface of the shoulder 132 prevents the needle 128 from passing back through the opening 170. When it is necessary to remove the needle 128 from the needle catch 122, the needle 128 may be moved toward an enlarged portion 174 of opening 172. The enlarged portion 174 is sized to allow the formed shoulder 132 to pass through without resistance. The needle catch 122 is preferably constructed of thin stainless steel of high temper, such as ANSI 301 full hard. The needle catch 122 may be fabricated by means of stamping, laser machining, or chemical etching.

The suturing instrument's component materials should be biocompatible. For example, the handle 102, the elongate body member 104, and portions of the needle deployment mechanism 110 may be fabricated from extruded, molded, or machined plastic material(s), such as polypropylene, polycarbonate, or glass-filled polycarbonate. Other components, for example the needle 128, may be made of stainless steel. Other suitable materials will be apparent to those skilled in the art. The material(s) used to form the suture should be biocompatible. The surgeon will select the length, diameter, and characteristics of the suture to suit a particular application. Additionally, the mechanical components and operation are similar in nature to those disclosed in U.S. Pat. Nos. 5,364,408 and 6,048,351, each of which is incorporated by reference herein in its entirety.

Referring to FIGS. 2A-2B and 4A-4E, the present invention enables a user to place multiple sutures 136 in a patient without removing the suturing instrument 100 from the patient. The user loads the suture 136c through the first suture slot 146a until the suture 136c emerges from the second suture slot 146b. The user then inserts the needle 128c through the needle input/output slot 142 into the needle compartment 140. The user repeats this process for additional sutures 136 and needles 128. The user can repeat this process for loading the first suture 136a and the first needle 128a, or the user can insert the first needle 128a directly into the needle carrier 124. In either case, the sutures 136a, 136b, 136c extend out of the second suture slot 146b. If the needle 128a is loaded into the needle compartment 140, the user pulls on the first suture 136a (held by the suture clip 144) to cause the first needle 128a to slide down an inclined needle shelf 204 and out of the needle compartment 140 through the needle output slot 142 into the lumen 138 of the needle carrier 124. The suture 136a extends out of the needle suture slot 148 and the second suture slot 146b.

In another embodiment, the suture 136a could be pulled by attaching the suture 136a to a spool mounted on the elongate body member 104 and winding the spool. In still other embodiments, the suture 136a could be pulled by other mechanical means known in the art, such as by a lever, for example. After the needles 128a, 128b, 128c and sutures 136a, 136b, 136c are loaded into the suturing instrument 100, portions of the sutures 136a, 136b, 136c extending out the suture slot 146b are held by the suture clip 144 (FIG. 1B). The needle carrier 124, which is part of the needle deployment mechanism 110, is sequentially connectable to the needles 128 stored in the needle compartment 140. This means that each needle 128 stored in the needle compartment 140 is connected to, and then deployed by, the needle carrier 124 one at a time in the order the needles 128 are dispensed from the needle compartment 140.

Figure 4A:
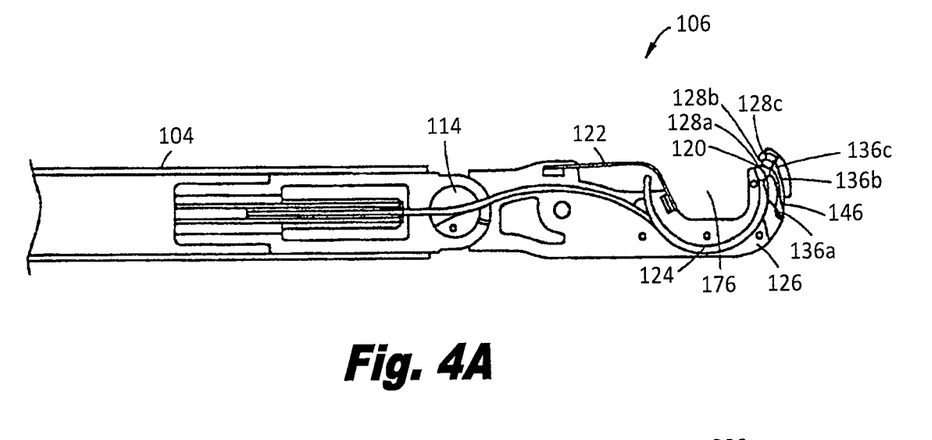
FIGS. 4A-4E are partial schematic cross-sectional views of the distal portion of the suturing instrument of FIG. 1A during various operational phases.
Figure 4B:
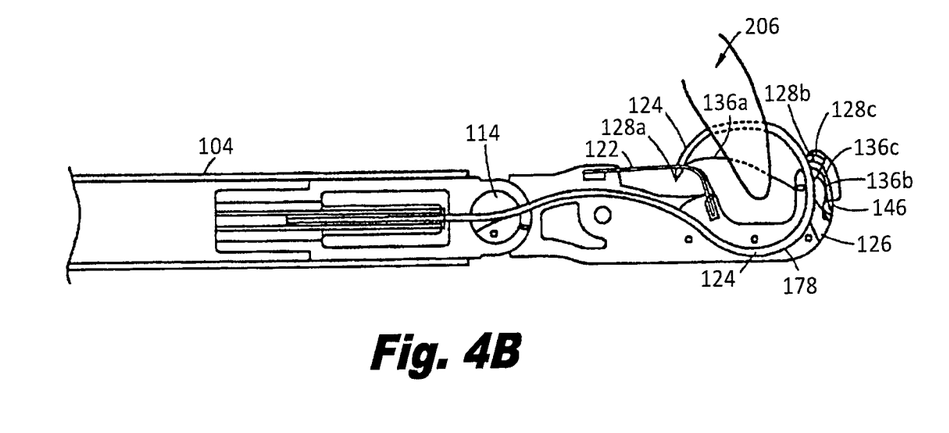

The user then inserts the elongate body member 104 into a patient and orients the elongate body member 104 so that the needle exit port 120 is proximate to or in contact with the tissue 206 to be sutured. The user then pushes the button 117 (FIG. 1B), as described above. Pushing the button 117 causes the needle carrier 124 (holding the first needle 128a) to extend out of the needle exit port 120 and push the needle 128a through the tissue 206. As the first needle 128a is pushed through the tissue 206, the first needle 128a pulls the first suture 136a through the tissue 206. As the user continues to push the button 117, the needle carrier 124 continues to advance out of the needle exit port 120 and directs the first needle 128a and the first suture 136a toward the needle catch 122. The user continues to push the button 117 until the first needle 128a contacts and becomes captured by the needle catch 122 (FIG. 4B). The user then retracts the needle carrier 124 by releasing the button 117, as previously described.

Figure 4C:
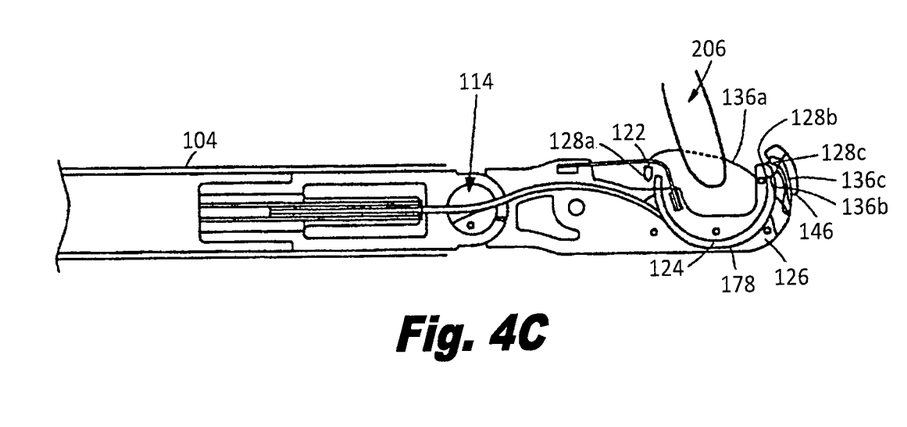
Figure 4D:
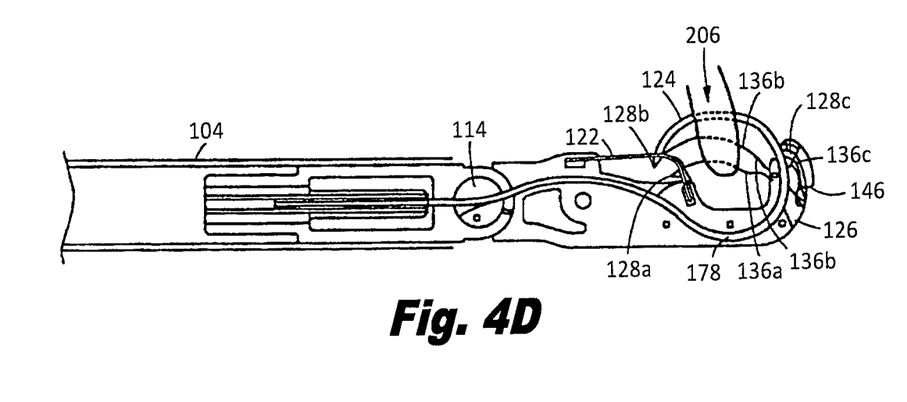
Figure 4E:
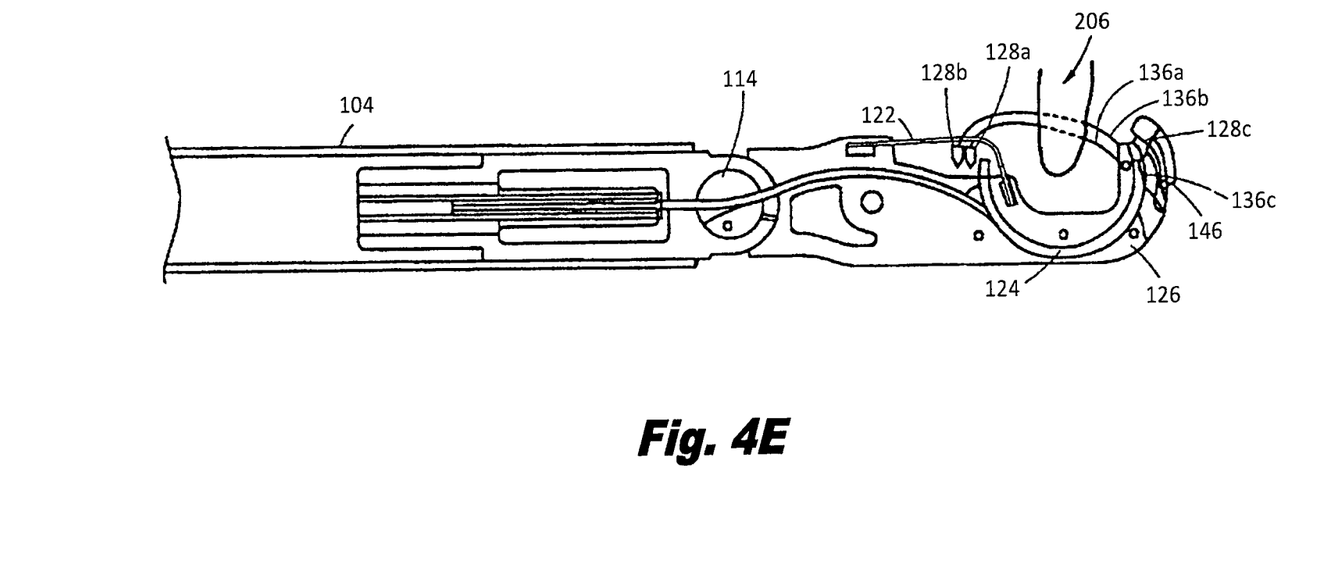

After the user retracts the needle carrier 124, the first needle 128a and the first suture 136a are left captured within the needle catch 122, with the first suture 136a extending through the tissue 206 (FIG. 4C). When the needle carrier 124 returns to a fully retracted position, the user pulls on the second suture 136b to cause the second needle 128b to slide down the inclined needle shelf 204 and out of the needle compartment 140 through the needle input/output slot 142 and into the lumen 138 of the needle carrier 124. The second suture 136b extends out of the needle carrier suture slot 148 and the second suture slot 146b. The user then advances the needle carrier 124 as described above until the second needle 128b is captured by the needle catch 122 (FIG. 4D). The user then retracts the needle carrier 124 as described above leaving the second needle 128b and the second suture 136b captured by the needle catch 122 (FIG. 4E). This procedure can be repeated for the third needle 128c, or for as many needles as may be stored in the needle compartment 140.

After one or more sutures 136 have been placed, the user withdraws the suturing instrument 100 from the patient. The user detaches the suture(s) 136 from the needle(s) 128 and ties a knot or knots into the suture(s) 136. The user can then use the knot pusher 184 to push the knot(s) into the patient as the knot(s) is tightened.

The suturing instrument 100 described herein can be used to pass sutures through bodily tissue during a procedure to repair uterine prolapse. Various methods for treating various pelvic dysfunctions including procedures to repair uterine prolapse have been described in U.S. Patent Application Ser. No. 61/017,257, filed Dec. 28, 2007 to Chu et al., which is incorporated herein by reference in its entirety. For example, one way to repair or correct uterine prolapse includes using sutures to suspend the uterus in an anatomically correct position. The uterus is suspended by sutures that are passed through the vaginal wall. In certain circumstances such as, for example, grade two prolapse (small prolapse), passing sutures through the vaginal wall with a free needle and needle driver is often difficult as there is limited space to work in. There are various delivery devices that can be used to insert or deliver a portion or all of an implant assembly into a pelvic region. A delivery device can be a suturing-type device that can be used to pass an end of a suture of an implant assembly through a pelvic tissue. The delivery device can be, for example, the Capio device manufactured by Boston Scientific Corporation (also referred to herein as a "Capio" or "Capio device" or "Capio delivery device"). An example of such a suturing delivery device is also described in U.S. Pat. No. 5,741,277 to Gordon et al., and U.S. Pat. No. 7,122,039 to Chu, the disclosures of which are hereby incorporated by reference in their entirety. The pelvic tissues can be, for example, a sacrospinous ligament, a tendineus arch of levator muscle, an obturator muscle, an iliococcygeus muscle or any other anatomical structure or tissue within a pelvis.

Figure 5:
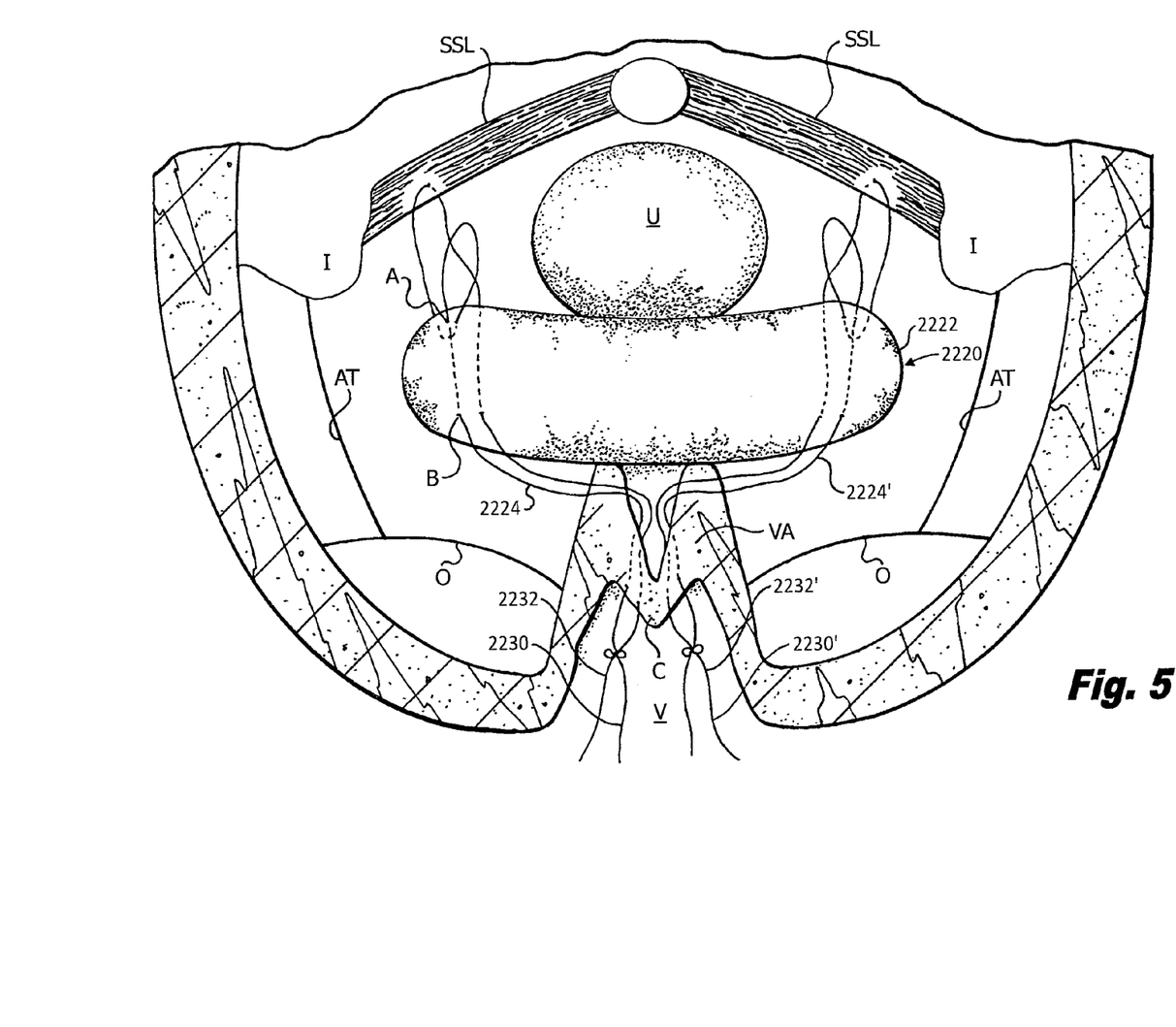
FIG. 5 is a front view of an implant assembly partially secured within a pelvic region of a patient.

Referring now to FIG. 5, a front view of a pelvic region is shown that includes a representation of a uterus U, sacrospinous ligaments SSL, a vagina V, a vaginal apex VA, the arcus tendineus AT, obturators O, ischial spines I, and a cervix C for reference. This embodiment illustrates an implant assembly 2220 that can be secured to the sacrospinous ligament SSL for repair of a grade two prolapse that can be delivered using suturing type delivery device (e.g., a Capio device). In this embodiment, the sutures 2224, 2224' are shown placed through the sacrospinous ligament SSL on opposites sides of the uterus U and the implant 2222 partially drawn to the sacrospinous ligament SSL. In an actual procedure, however, when the loop or noose 2240, 2240' is closed or tightened, the implant 2222 would be in contact with the sacrospinous ligament. As the sutures 2224, 2224' are tightened and knotted to the vaginal apex VA, a device, such as a tenaculum clamp, can be used to move or approximate the vaginal apex VA to the uterus U. In this embodiment, the ends 2232, 2230 of the sutures 2224, 2224' are passed through the wall of the vaginal apex VA for securement thereto. A first knot can be tied in the vagina after the sutures have been tensioned. A physician can use a finger to push the knot down into the vagina V, as well as to assist in repositioning the vagina deep in the pelvic region. During the procedure, a backstop can be inserted between the bodily tissue and another portion of the body, such as the bladder of the patient, to prevent inadvertent puncture of such other portion of the body.

Methods by which a suture is passed through the entire vaginal wall and knotted within the vaginal lumen may not be desirable if the patient is sexually active. One alternative is to use absorbable sutures such that the knots would be absorbed during the healing period, however this does not provide a permanent solution in cases where tissue ingrowth is weak.

Figure 6A:
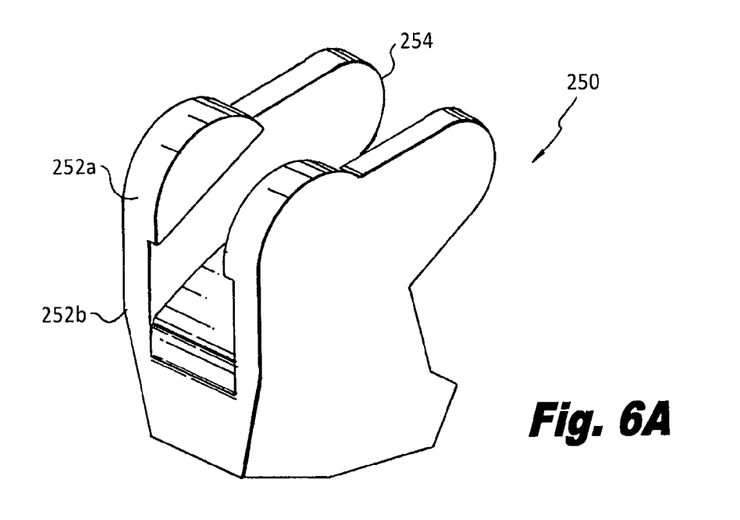
FIG. 6A. is a schematic perspective view of a depth adaptor for use with the suturing instrument of FIG. 1A.
Figure 6B:
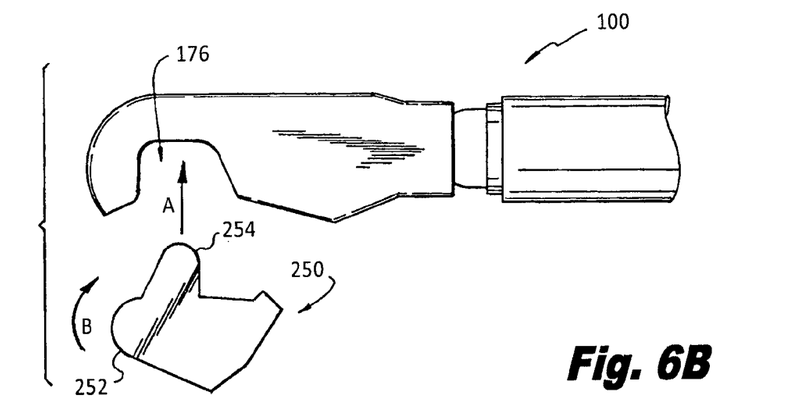
FIG. 6B is a side view of the depth adaptor of FIG. 6A being inserted into a suturing instrument.
Figure 6C:
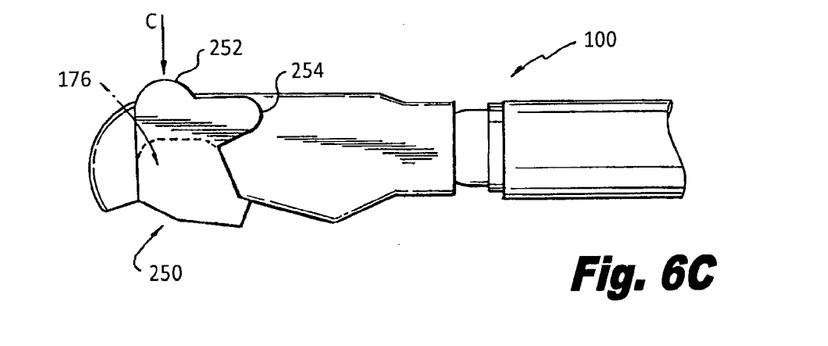
FIG. 6C is a side view of a suturing instrument with the depth adaptor in place.

Referring now to FIGS. 6A-6C, an adaptor 250 is shown to be used in conjunction with the suturing instrument 100 to control the depth of bite of the suture. For example, in certain uterine preservation procedures, the adaptor 250 can be used with the suturing instrument 100 to pass the suture through the internal epithelium of the vaginal wall and not through the entire thickness of the vaginal wall such that the two ends of the suture are knotted within the anterior incision to approximate the vaginal apex and the sacrospinous ligament. Permanent sutures can be used in this case to provide a permanent approximation between the vaginal apex and sacrospinous ligament. In cases where tissue ingrowth is weak, permanent sutures maintain the approximation of the vagina apex and sacrospinous ligament unless absorbable sutures. In addition, sutures and suture knots that are not exposed in the vaginal lumen are more likely not to develop complications such as points of infection or points of erosions.

FIG. 6B illustrates one embodiment of the adaptor 250 shown being inserted into the opening 176 of the suturing instrument 100. As shown, the adaptor 250 has two snaps 252*a*, 252*b* (collectively 252) to secure it in place. The leading edge 254 is inserted into the opening 176 in the direction indicated by arrow A. Then it is rotated in the opening 176 in the direction indicated by arrow B until the snaps 252 engage the suturing instrument 100. FIG. 6C illustrates the suturing instrument 100 with the depth adaptor 250 in place. The adaptor 250 can be removed from the suturing instrument 100 by depressing the snaps 252 in the direction indicated by arrow C and then rotating the adaptor 250 in the opposite direction of arrow B. The adaptor 250 can be made from a biocompatible material such as, for example, extruded, molded, or machined plastic material(s), such as polypropylene, polycarbonate, or glass-filled polycarbonate. Furthermore, additional sizes and shapes can be used, as well as different attachment mechanisms to secure the adaptor 250 in the opening 176.

Figure 7:
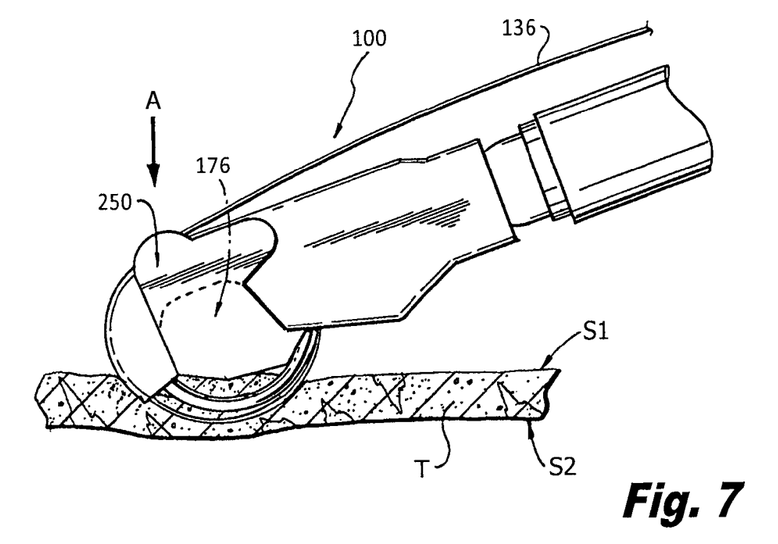
FIG. 7 is a side view of a suturing instrument with the depth adaptor in place being used to place a suture through the vaginal wall.

FIG. 7 illustrates the suturing instrument 100 with the adaptor 250 in place being used to place a suture through the vaginal wall. During use, the suturing instrument 100 is pressed against the tissue T to be sutured (as indicated by arrow A in FIG. 7) and the adaptor 250 prevents the tissue T from entering the opening 176, thus controlling the depth of bite of the needle carrier 124. In this embodiment the adaptor 250 is sized such that the needle carrier 124 does not penetrate through the entire thickness T of the vaginal wall. The suture is shown entering on side 1 S1 of the tissue T, not penetrating through side 2 S2, and exiting back through side 1 S1. In other embodiments the adaptor 250 is sized to penetrate through the entire thickness T of the vaginal wall i.e., the suture can enter the tissue T at side 1 S1, exit side 2 S2, reenter side 2 S2, and exit at side 1 S1. In other embodiments the adaptor 250 is sized to control the depth of penetration (i.e., depth of bite) into tissue, for example, to prevent inadvertent punctures into bones, organs, tendons, or other tissue. The adaptor 250 can be opaque, translucent, or transparent to allow for visualization in placement of the suturing device onto tissue. In alternative embodiments, the suturing instrument can include a plurality of adaptors 250 that can include color coding or other markings to identify its size or penetrating depth.

In one example of a uterine preservation procedure, the suturing instrument 100 is used to access and place a suture through the sacrospinous ligament on one side of the pelvic region without the adaptor 250 in place. The adaptor 250 is then inserted into the device to aid in the placement of the suture into the vaginal apex. As described above, the adaptor 250 prevents the needle carrier 124 from passing too deep, or entirely though the vaginal wall at the apex. The procedure is then repeated with a second suture on the other side of the pelvic region. Suspension of the vagina by the vaginal apex to the sacrospinous ligament after vaginal surgery will aid in the patient's recovery, preventing inadvertent movement or displacement of the vagina during the healing or tissue ingrowth period. The suturing instrument 100 with the adaptor 250 is not limited for use in uterine prolapse procedure and can be used in other pelvic floor repairs such as vaginal vault prolapse and cystocele repair or various other surgical procedures.

Figure 8:
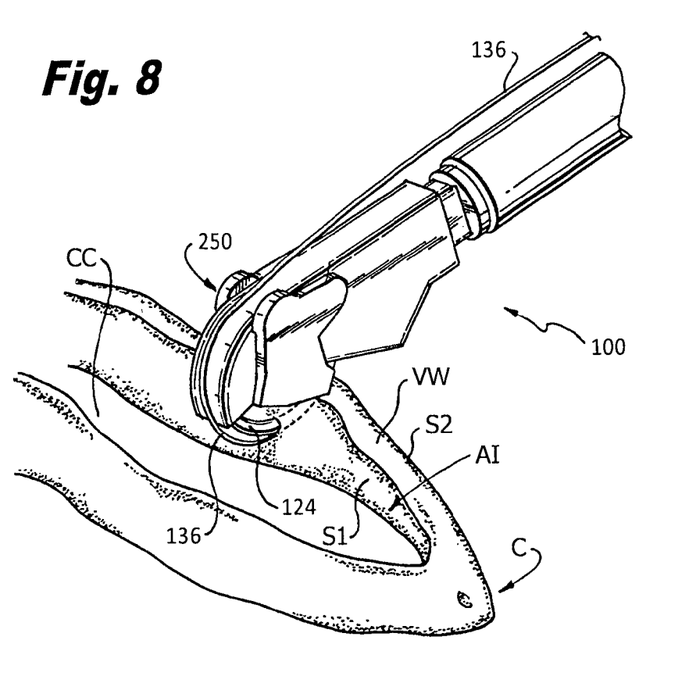
FIG. 8 is a schematic view of a suturing instrument with the depth adaptor in place being used in a uterine preservation procedure.

FIG. 8 is an illustration of the suturing instrument 100 with the adaptor 250 in place being used during a uterine preservation procedure to suture to the vaginal apex. The vagina is shown prolapsed (and inverted) with an anterior incision AI made. With the suture 136 loaded suturing instrument 100 is placed into the anterior incision AI and positioned over the intended target such as, for example, 2 centimeters lateral to the midline of the cervix C. The needle deployment mechanism is activated to place the suture 136 through side 1 S1 of the vaginal wall VW, but not through side 2 S2, and then exits back through to side 1 S1. In this embodiment, side 1 S1 is the interior side of the anterior incision AI where the knot can be tied to secure the vaginal apex to the sacrospinous ligament.

Other embodiments incorporating the concepts disclosed herein may be used without departing from the spirit and scope of the invention. The described embodiments are to be considered in all respects as only illustrative and not restrictive.

What is claimed is:

1. A method comprising:
   securing a first suture to a first sacrospinous ligament on a first side of a pelvic region of a patient;
   securing a second suture to a second sacrospinous ligament on a second side of the pelvic region, opposite the first side of the pelvic region;
   securing the first suture to a vaginal apex of the patient at a first location;
   securing the second suture to the vaginal apex at a second location; and
   tensioning the first and second sutures such that the vaginal apex is approximated to the first sacrospinous ligament and the second sacrospinous ligament,
   wherein securing the first suture to the vaginal apex at the first location and securing the second suture to the vaginal apex at the second location include coupling an adaptor to a suturing instrument, the adaptor preventing a needle carrier of the suturing instrument from passing entirely through a thickness of a vaginal wall.

2. The method claim 1, wherein securing the first suture to the first sacrospinous ligament includes inserting the suturing instrument without the adaptor into a body of the patient and placing the first suture through the first sacrospinous ligament.

3. The method of claim 1, wherein securing the first suture to the vaginal apex includes placing the first suture through a first side of the vaginal wall where the first suture exits back through the first side of the vaginal wall such that the first suture does not extend through a second side of the vaginal wall, wherein a distance between the first side of the vaginal wall and the second side of the vaginal wall define the thickness of the vaginal wall.

4. The method of claim 1, wherein the first suture is a non-absorbable suture.

5. The method of claim 1, wherein the second suture is a non-absorbable suture.

6. The method of claim 1, wherein securing the first suture to the vaginal apex includes passing the first suture through an internal epithelium of the vaginal wall such that two ends of the first suture are knotted within an anterior incision to approximate the vaginal apex and the first sacrospinous ligament.

7. The method of claim 1, wherein coupling the adaptor to the suturing instrument includes inserting the adaptor into an opening on the suturing instrument, the opening being disposed between a needle exit port of the suturing instrument and a needle catch of the suturing instrument.

8. The method of claim 7, wherein inserting the adaptor into the opening on the suturing instrument includes inserting a leading edge of the adaptor into the opening and rotating the adaptor in the opening in a first direction until a coupling portion of the adaptor engages with the suturing instrument.

9. The method of claim 8, further comprising:
de-coupling the adaptor from the suturing instrument by depressing the coupling portion and rotating the adaptor in a second direction, the second direction being opposite to the first direction.

10. The method of claim 1, wherein the adaptor includes a first side portion and a second side portion, the first side portion defining a first coupling portion configured to engage with the suturing instrument, the second side portion defining a second coupling portion configured to engage with the suturing instrument.

11. A method comprising:
securing, with a suturing instrument, a first suture to first bodily tissue on a first side of a pelvic region of a patient;
securing, with the suturing instrument, a second suture to second bodily tissue on a second side of the pelvic region, opposite the first side of the pelvic region;
coupling an adaptor within an opening on the suturing instrument, the opening configured to receive tissue, and the adaptor controls a depth of penetration into the tissue;
securing, with the suturing instrument coupled to the adaptor, the first suture to a vaginal wall of the patient at a first location; and
securing, with the suturing instrument coupled to the adaptor, the second suture to the vaginal wall at a second location,
wherein the adaptor prevents a needle carrier of the suturing instrument from passing entirely through a thickness of the vaginal wall.

12. The method of claim 11, further comprising:
tensioning the first and second sutures such that a vaginal apex is approximated to the first bodily tissue and the second bodily tissue.

13. The method of claim 11, wherein the first bodily tissue includes a first sacrospinous ligament and the second bodily tissue includes a second sacrospinous ligament.

14. The method claim 11,
wherein securing the first suture to the first bodily tissue includes inserting the suturing instrument without the adaptor into a body of the patient and placing the first suture through the first bodily tissue,
wherein securing the second suture to the second bodily tissue includes inserting the suturing instrument without the adaptor into the body of the patient and placing the second suture through the second bodily tissue.

15. The method of claim 11, wherein the first suture and the second suture are non-absorbable sutures.

16. The method of claim 11, wherein the opening is disposed between a needle exit port of the suturing instrument and a needle catch of the suturing instrument.

17. The method of claim 11, wherein coupling the adaptor to the suturing instrument includes inserting a leading edge of the adaptor into the opening and rotating the adaptor in the opening in a first direction until a coupling portion of the adaptor engages with the suturing instrument.

18. The method of claim 17, wherein the coupling portion includes a snap member.

19. The method of claim 17, further comprising:
de-coupling the adaptor from the suturing instrument by depressing the coupling portion and rotating the adaptor in a second direction, the second direction being opposite to the first direction.

\* \* \* \* \*